US00PP15925P3

(12) United States Plant Patent

Ranney et al.

(10) Patent No.: US PP15,925 P3

(45) Date of Patent: Aug. 23, 2005

(54) **HYBRID *CALYCANTHUS* PLANT NAMED 'VENUS'**

(50) Latin Name: ***Calycanthus* (*chinensis*×*floridus*)× *Calycanthus* (*chinensis*×*occidentalis*)**
Varietal Denomination: Venus

(75) Inventors: Thomas Ranney, Arden, NC (US); Thomas Eaker, Hendersonville, NC (US)

(73) Assignee: North Carolina State University, Raleigh, NC (US)

( * ) Notice: Subject to any disclaimer, the term of this patent is extended or adjusted under 35 U.S.C. 154(b) by 138 days.

(21) Appl. No.: 10/615,861

(22) Filed: Jul. 9, 2003

(65) Prior Publication Data

US 2005/0010984 P1 Jan. 13, 2005

(51) Int. Cl.[7] ..... A01H 5/00

(52) U.S. Cl. ..... Plt./226

(58) Field of Search ..... Plt./226

(56) References Cited

PUBLICATIONS

"*Calycanthus chinensis*" *Kemper Center for Home Gardening* http://ridgwaydb.mobot.org/kemperweb/plantfinder/plant.asp?code=m380 Date of access Oct. 10, 2003.

"*Calycanthus floridus* Athens" http://www.nobleplants.com/introductions/calycanthus.htm Date of access Oct. 10, 2003.

"Sweet shrub Calycanthacceae *Calycanthus occidentalis*" http://www.cnr.vt.edu/dendro/dendrology/syllabus2/occidentalis.htm Date of access Oct. 10, 2003.

Ranney et al., "Breeding and Developing New Nursery Crops Progress Report, 2002" North Carolina State University, Aug. 28, 2002.

Ranney, Thomas G., "Inventing New Plants" Oral Presentation, Southern Nursery Association Trade Show, Atlanta, Georgia, Aug. 2, 2002.

*Primary Examiner*—Kent Bell

(74) *Attorney, Agent, or Firm*—Myers Bigel Sibley & Sajovec, P.A.

(57) ABSTRACT

*Calycanthus* cultivar 'Venus' is a medium-sized, multi-stemmed shrub producing large, yellow-green flower buds that open to unique large, white magnolia-like flowers with yellow and purple infusions in the center. The flowers open widely, such that all of the tepals are visible, and are fragrant with the fruity aroma of strawberries and melons.

3 Drawing Sheets

Latin name of the genus and species: The Latin name of the novel hybrid cultivar disclosed herein is *Calycanthus* (*chinensis*×*floridus*)×*Calycanthus* (*chinensis*×*occidentalis*) 'Venus'.

Variety denomination: The *Calycanthus* hybrid disclosed herein has been given the variety denomination 'Venus'.

BACKGROUND OF THE INVENTION

*Calycanthus* are deciduous shrubs that are commonly grown as ornamental landscape plants. There are three species of *Calycanthus*. *Calycanthus floridus* (common sweetshrub, Carolina allspice, Carolina sweetshrub, strawberry-shrub, bubby blossom, sweet bubby, sweet Bettie, spicebush) is found throughout much of the Eastern United States and commonly grows as an understory shrub in mixed deciduous forests, often along streams and in moist woodlands. Plant height can vary and ranges from 1 to 2.5 meters, growing as multi-stemmed shrubs with suckering shoots arising from the base and roots. Fall color can be an attractive buttery yellow. The flowers range in size (2–3 cm across) with tepals that vary from reddish purple to a dark chocolate brown. The fragrance is variable, but can have a pleasant fruity aroma. Older synonyms for this species include *Calycanthus glaucus, C. fertilis, C. floridus* var. *laevigatus, C. floridus* var. *oblongifolius, C. nanus, C. brockianus,* and *C. mohrii.*

*Calycanthus occidentalis* (California sweetshrub) is naturally found in Washington and California growing as an understory species along streams and on moist canyon slopes. Although similar to the Carolina sweetshrub, the California species is larger in almost all respects with the plants growing to over 3.5 meters tall. The flowers, although slightly larger (2 to 4 cm across) and a brighter red, are typically not as fragrant as those produced by *C. floridus.*

The Chinese wax shrub *Calycanthus chinensis* (*Sinocalycanthus chinensis*) is a rare species native to the Zheijang Province in southeast China. This medium-sized shrub grows to 1 to 2.7 meters tall with large, glossy leaves. The flowers open more completely (up to 8 cm in diameter) than do North American species and are multicolored with the outer perianth whorl being whitish pink and the inner whorl being a strong yellow with occasional purple streaks at the base, with no fragrance.

*Calycanthus* is becoming increasingly popular as a landscape plant for use as a shrub border, foundation plant or a naturalizing plant. *Calycanthus* has few disease or insect pest problems. Several horticultural varieties of *Calycanthus floridus* are known including 'Athens' (unpatented), 'Edith Wilder' (unpatented), and 'Michael Linsey' (unpatented). As far as the inventors are aware, no varieties of *Calycanthus* are patented.

The present invention relates to a new and distinct hybrid variety of *Calycanthus* which is known botanically as *Calycanthus* L. 'Venus' (×*Sinocalycalycanthus* 'Venus' Lasseigne and Fantz) and has been given the cultivar name 'Venus'. *Calycanthus* 'Venus' is suitable for use as a medium-sized ornamental landscape shrub.

There is some disagreement about the classification of the Chinese wax shrub. Some consider that the proper classification is in the genus *Calycanthus* (i.e., *Calycanthus chinensis,* W. C. Cheng and S. Y. Chang); but another treatment places it in a separate genus (*Sinocalycanthus chinensis,* W. C. Cheng and S. Y. Chang). However, recent molecular phylogeny data (Zhou, S., S. Renner, and J. Wen. Molecular phylogeny and inter and intracontinental biogeography of *Calycanthaceae. In Preparation*) has indicated that this species is genetically embedded among other *Calycanthus* species providing strong justification to place the Asian species within the genus *Calycanthus.* Based on this treatment, the proper scientific name for the hybrid of the invention is: *Calycanthus* L. 'Venus'. If future taxonomic treatments place the Chinese wax shrub into the genus *Sinocalycanthus,* then the proper scientific name for this new hybrid would be: ×*Sinocalycalycanthus* Lasseigne and Fantz 'Venus'.

Parentage. *Calycanthus* cultivar 'Venus' resulted from controlled pollinations using three different species (female parents are listed first for each combination; see FIG. 4):

H2000-14-001 (*Calycanthus chinensis*×*Calycanthus floridus* 'Athens') [unpatented]×H2000-17-002 (*Calycanthus chinensis*×*Calycanthus occidentalis*) [unpatented].

*Calycanthus* 'Venus' originated from a controlled breeding program, and was selected from seed germinated in the Fall of 2001 in a cultivated area at the North Carolina State University, Mountain Horticultural Crops Research Station, Fletcher, N.C., USA.

Asexual reproduction. The first asexual propagation of 'Venus' was carried out in June, 2002 by rooting stem cuttings at North Carolina State University, Mountain Horticultural Crops Research Station, Fletcher, N.C., USA. *Calycanthus* cultivar 'Venus' roots readily (>90%) from firm, subterminal, softwood cuttings when treated with a basal dip of 5,000–10,000 ppm indole butyric acid (potassium salt) in water. The combination of distinguishing characteristics disclosed herein for 'Venus' have remained stable and true to type through successive cycles of asexual propagation.

SUMMARY OF THE INVENTION

*Calycanthus* cultivar 'Venus' is a medium-sized, multi-stemmed shrub producing large, yellow-green flower buds that open to unique large, white magnolia-like flowers with yellow and purple infusions in the center. The flowers open widely, such that all of the tepals are visible, and are fragrant with the fruity aroma of strawberries and melons.

This combination of traits has been consistently observed and distinguishes 'Venus' from the parental species as well as other commercial cultivars known to the inventors.

BRIEF DESCRIPTION OF THE DRAWINGS

The accompanying photographs exemplify the distinguishing traits of the new *Calycanthus* 'Venus'. All photographs are of greenhouse-grown plants in Fletcher, N.C. The photographs were produced using conventional techniques and although colors may appear different from actual colors due to lighting and the equipment used, they are as accurate as possible by conventional photography.

DETAILED BOTANICAL DESCRIPTION

The following is a detailed description of the botanical characteristics of the new and distinct *Calycanthus* cultivar 'Venus'. Color determinations are in accordance with the 2001 Edition of The Royal Horticultural Society Colour chart. Where dimensions, sizes, color and other characteristics are given, it is to be understood that such characteristics are approximations of averages and ranges as measured under growing conditions in Fletcher, N.C. and are as accurately reported as practicable.

The following description of 'Venus' is from 18 month-old plants grown in a greenhouse in Spring, 2003. *Calycanthus* 'Venus' has not been observed under all possible conditions; it will be appreciated that phenotypic differences may occur with variations in environmental, climactic and cultural conditions.

Figure 1:
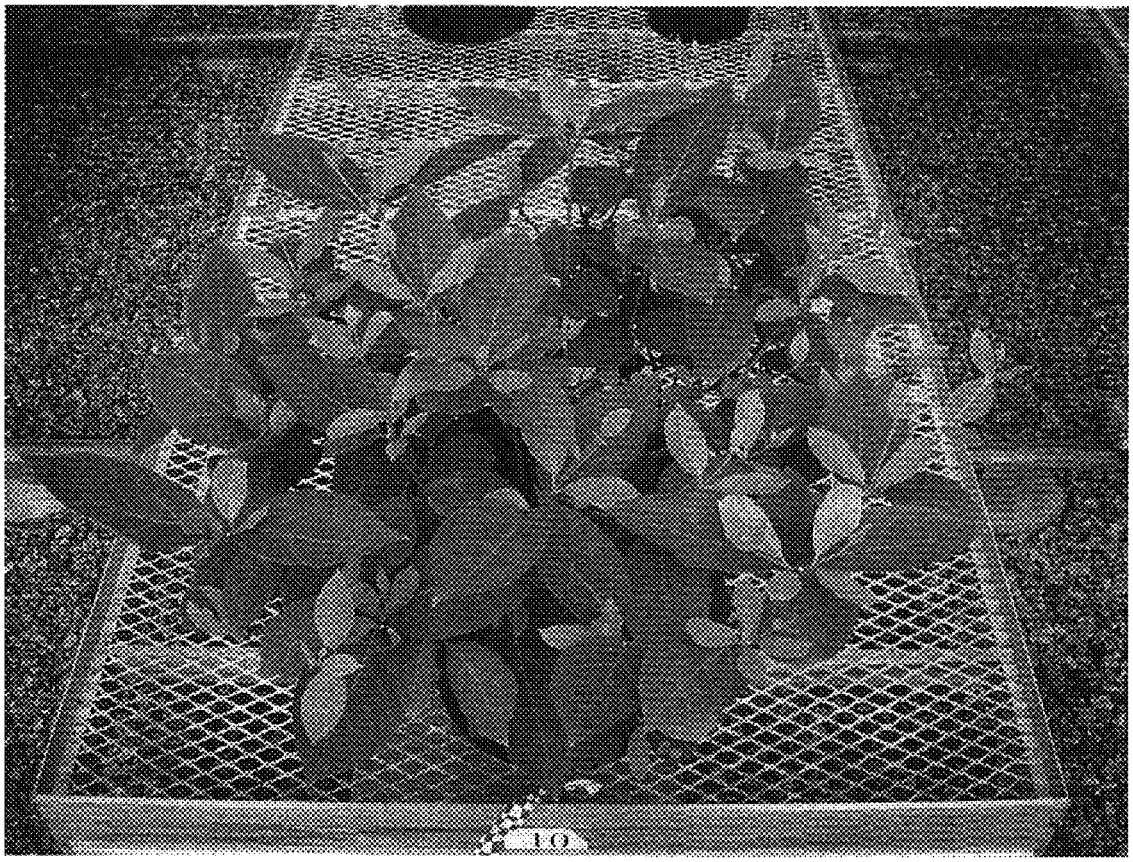
FIG. 1 is a top view of the original plant growing in a 7-gallon container at approximately 18-months of age.

Classification: Shrub
Type: Deciduous
Form: Multi-stemmed shrub
Shape: Rounded to spreading
Size: Size at maturity is not yet known. The most mature specimen of the variety is 75 cm tall and 75 cm wide at 1.5 years of age (FIG. 1). Based on this specimen's observed growth rate and the size of its parents, 'Venus' is anticipated to be a medium-sized shrub reaching 1.5 to 2.5 meters in height.
Vigor: Growth rate is moderate. Vegetative shoots typically grow 25 to 75 cm per growing season. Flowering shoots typically grow 10 to 15 cm before flowering.
Shoots: Young shoots are glabrous and yellow-green (ranging from 144A to 144B) to green (ranging from 143A to 143B) with faint white lenticels (155 C). Opposite or sub-opposite arrangement. Typical shoot length: 25 to 75 cm; typical shoot diameter: 4 to 8 mm; typical internode length: 3 to 9 cm.
Bark: Branches and trunk have greyed-green bark (ranging from 197B to 197D) with greyed-orange lenticels (ranging from 165C to 165D).
Trunk: Typical trunk diameter of an 18 month-old plant is 1 to 2 cm measured 2 cm above the soil.
Branches: Typical branch length of an 18 month-old plant: 30 to 65 cm; typical branch diameter: 6 to 10 mm.
Foliage:
*Size.*—Leaves vary considerably in size depending on the environment and time of year, but typically range from 7 to 20 cm in length and 5 to 10 cm in width.
*Form.*—Simple. Opposite or sub-opposite in arrangement. Shape elliptical to ovate. Apex acuminate. Base rounded to acute, rarely slightly oblique.
*Margin.*—Entire.
*Veination.*—5 to 7 pairs of veins (opposite).
*Surface.*—Slightly scabrous above (adaxial). Glabrous below (abaxial).
*Petioles.*—Range from 1 to 1.5 cm in length, 1 to 2 mm in diameter and are slightly pubescent. Typical petiole color is yellow-green (145A).
*Summer color.*—Young leaves are yellow-green (ranging from 144A to 144B) to green (ranging from 143A to 143B) and glossy. Mature leaves are green (ranging from 137A to 137C) on adaxial (somewhat glossy) and abaxial (dull, glaucescent) sides.

*Fall color.*—Fall foliage ranges from a buttery yellow (ranging from 11C to 11D) to brown-yellow (ranging from 24C to 24D) with some greyed-orange (ranging from N167C to N167D) for both upper and lower leaf surfaces.

Inflorescence: *Calycanthus* 'Venus' produces solitary, complete flowers with 20 to 30 tepals in one imbricate series on a 10 to 20 mm stalk at the terminals of current season's growth. These flowers are magnolia-like and open fully such that all of the tepals are visible.

Figure 2:
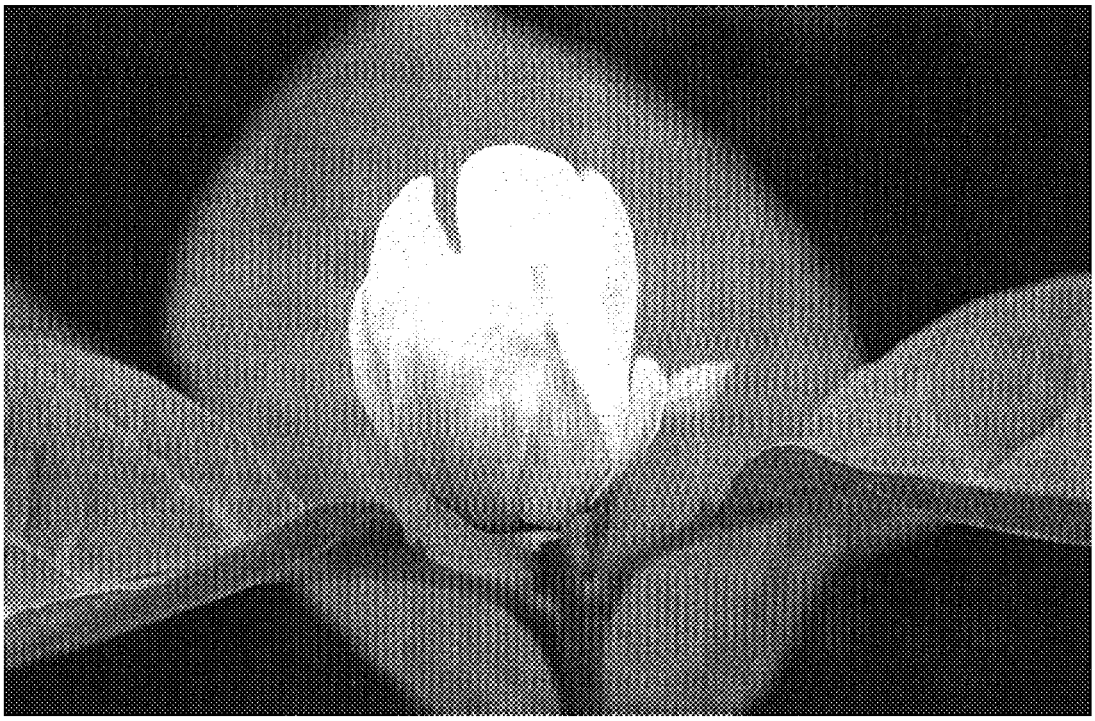
FIG. 2 is a side view of the flower bud.

Flower buds (FIG. 2):

*Size and shape.*—Ellipsoid, 2 to 3.5 cm in length and 2 cm in diameter.

*Color.*—Outer tepals are primarily green-yellow (1D) with some yellow-green (ranging from 144C to 144D).

Figure 3:
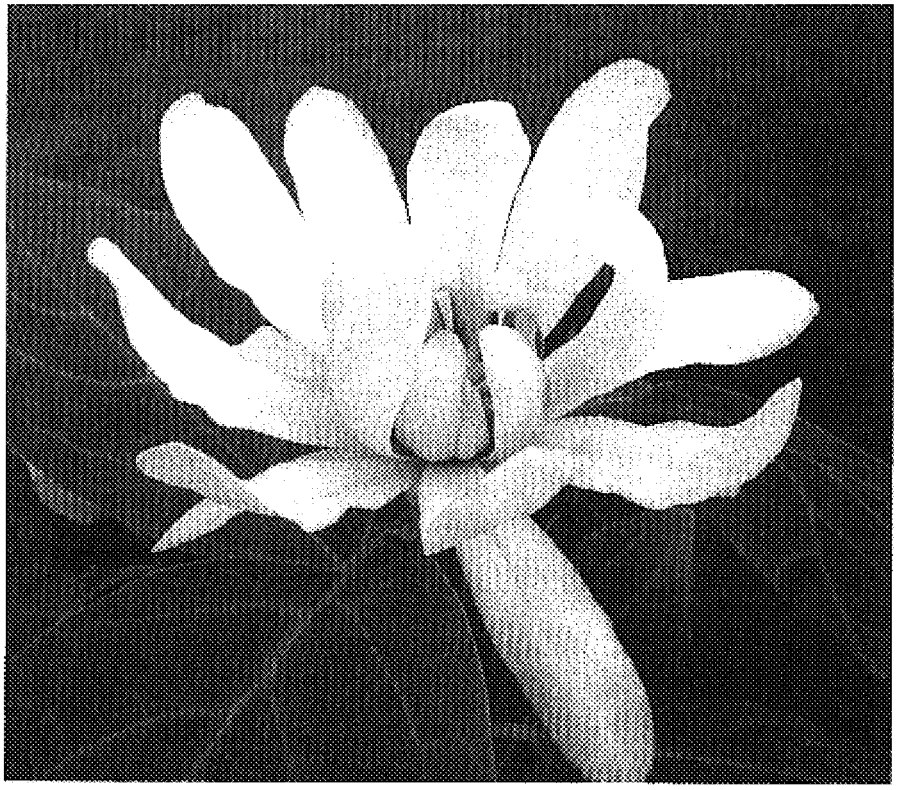
FIG. 3 illustrates the open flower.

Open flowers (FIG. 3):

*Flower size.*—Ranges from 7.5 to 11.5 cm in diameter. Flower depth ranges from 3 to 5 cm.

*Color.*—Upper surface of outer (distal) tepals is primarily white (ranging from 155A to 155D) with some green-yellow (1D). Lower surface of outer tepals is white (ranging from 155A to 155D) with some green-yellow (1D) and yellow-green (ranging from 144C to 144D). Upper surface of inner (proximal) tepals is white (ranging from 155A to 155D) and yellow (5C) with a slight blush of red-purple (60C) on edges and base. The lower surface of the inner tepals is similar to the upper surface in color, but with less red-purple (60C).

*Bracts.*—One to two bracts subtending flowers; shape: lanceolate; length: 1 to 1.5 cm; width: 5 to 7 mm; apex: acuminate; base: cuneate; color: green (ranging from 137A to 137C) on both surfaces. Margin is entire.

Fragrance: Fruity aroma similar to ripe strawberries and melons.

Peduncle: Peduncles range from 1 to 2 cm in length and 2 to 4 mm in diameter. Color is green (ranging from 143C to 144B) with a blush of red (44C) on upper surface.

Bloom time: In Fletcher, N.C., flowers begin to bloom in early May and continue sporadically throughout June and July. Lastingness of bloom ranges from 2 to 4 days.

Fruit: Fruit have not been observed even with controlled pollination.

Reproductive structures:

*Pistils.*—Filamentous with no clear distinction between stigma and style, translucent, 4 to 5 mm in length, 7 to 15 pistils per flower.

*Stamens.*—Ten to 20 stamens per flower. Anthers range from 4 to 6 mm in length; filament ranges from 0.5 to 1.5 mm in length. Anthers are yellow (11B), and filaments are green-yellow (1D).

*Ovary.*—Ranges from 7 to 12 mm in length, 7 to 15 mm in width. Color is yellow-green (ranging from 145A to 145D), 1 ovary per flower.

*Pollen.*—Fusiform to rounded in shape, 0.03 to 0.06 mm in length, 0.02 to 0.05 mm in width. Pollen is yellow (11B), translucent to slightly opaque.

Cultural requirements, disease and pest resistance/susceptibility: Cultural requirements, disease and pest resistance/susceptibility for *Calycanthus* 'Venus' appear to be similar to other *Calycanthus.* No unique problems have been found for this plant, and no particular resistance or susceptibility to disease or pests has been observed. This variety can be grown in full-sun to shade with best growth on moist sites that do not become overly dry. *Calycanthus* 'Venus' tolerates a range of soil pH from about 4.5 to 6.5.

Cold hardiness: Based on the parent species, 'Venus' is estimated to be cold hardy in USDA zones 5–9. 'Venus' specimens have been observed to survive at 0° F.

Figure 4:
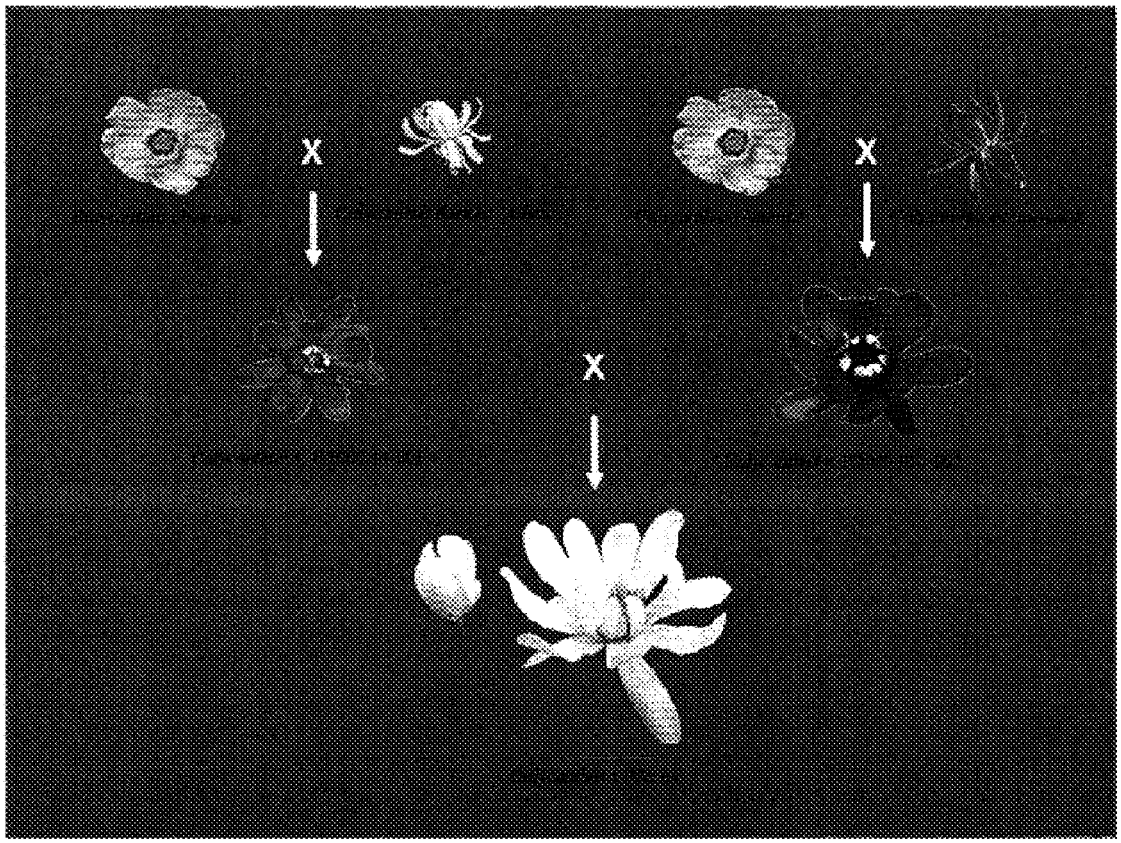
FIG. 4 illustrates the pedigree of *Calycanthus* 'Venus' including flowers of 'Venus' as well as progenitor varieties. Female parents are listed first for each cross.

Comparison with related species: *Calycanthus* cultivar 'Venus' has a combination of traits that produces a more attractive, fragrant ornamental shrub as compared with other *Calycanthus* species. In particular, 'Venus' produces a large, white magnolia-like flower that is unique among *Calycanthus.* 'Venus' can be readily distinguished from the parental species by the combination of size, color, shape, habit and fragrance of its flowers (see, e.g., FIG. 4). For example, *Calycanthus floridus* (including the 'Athens' cultivar) produces a relatively small, sometimes fragrant maroon to yellow-green flower, which does not completely open. *Calycanthus occidentalis* also produces a relatively small (as compared with 'Venus') brown to reddish-brown flower, which does not open and which has little or no fragrance. The *C. chinensis* species has a larger (as compared with *C. floridus* and *C. occidentalis*), flat opened flower, which has no fragrance. In contrast, 'Venus' produces very large magnolia-like flowers which are unique among *Calycanthus,* have a strong fragrance, and are held up above the foliage. The flowers are white with yellow and purple infusions at the center. Further comparisons are provided in Table 1.

TABLE 1

Comparison with Related Species

| Characteristic | *Calycanthus* 'Venus' | *Calycanthus floridus* | *Calycanthus occidentalis* | *Calycanthus chinensis* |
|---|---|---|---|---|
| Size of Flower | 7.5–11.5 cm. | 2–3 cm. | 2–4 cm. | 5–8 cm. |
| Color of Flower | Outer tepals: Upper surface is white with some green-yellow; lower surface is white with some green-yellow and yellow-green. Inner tepals: Upper surface is white and yellow with a slight blush of red-purple on edges and base; lower surface is similar, but with less red-purple. | Typically reddish-brown. Yellow-green for 'Athens'. | Reddish-brown. | Outer tepals whitish-pink. Inner tepals yellow. |
| Flower Fragrance | Fruity. | Variable. Often fruity. | Little or none. | None. |
| Tepal Arrangement | Imbricate. | Imbricate. | Imbricate. | Two-series. |

Comparison with parental cultivars: 'Venus' is easily distinguished from either parent based on open flower color (see, FIG. 4). Flowers of the female parent H2000-14-001 have greyed-purple (183A) tepals (both surfaces) with pale yellow (4C) tips on the innermost tepals. Flowers of the male parent H2000-17-002 have red-purple (59B) tepals (both surfaces) with distinct yellow (ranging from 4A to 4B) tips on the innermost tepals. Flowers of 'Venus' are primarily white with some green-yellow, yellow, yellow-green and red-purple as described above under "Open Flowers, Color" and in Table 1 (see also, FIG. 3).

What is claimed is:

1. A new and distinct hybrid cultivar of *Calycanthus* plant named 'Venus', substantially as illustrated and described herein.

* * * * *